United States Patent [19]

Kronheim

[11] Patent Number: 4,801,686

[45] Date of Patent: Jan. 31, 1989

[54] PURIFICATION OF RECOMBINANT INTERLEUKIN-1

[75] Inventor: Shirley R. Kronheim, Seattle, Wash.

[73] Assignee: Immunex Corporation, Seattle, Wash.

[21] Appl. No.: 908,426

[22] Filed: Sep. 4, 1986

[51] Int. Cl.[4] ............................ C07K 3/12; C07K 3/28
[52] U.S. Cl. .................................... 530/351; 530/412; 530/413; 530/414; 530/416; 530/417; 530/422; 435/68; 435/803
[58] Field of Search ............... 530/351, 412, 413, 414, 530/416, 417, 422; 435/68, 803

[56] References Cited

U.S. PATENT DOCUMENTS

| | | | |
|---|---|---|---|
| 4,675,387 | 6/1987 | Rorant | 424/85 |
| 4,711,842 | 12/1987 | Taniyama et al. | 435/68 |
| 4,762,914 | 8/1988 | Auron et al. | 530/351 |
| 4,774,320 | 9/1988 | Iagliabue | 530/351 |

FOREIGN PATENT DOCUMENTS

| | | |
|---|---|---|
| 0114506 | 8/1984 | European Pat. Off. . |
| 3432196 | 3/1986 | Fed. Rep. of Germany ........ 435/68 |
| 0149386 | 8/1985 | Japan . |

OTHER PUBLICATIONS

Kronheim et al., "Human Interleukin 1", *J. Exp. Med.* 161:490 (1985).
Durum et al., "Interleukin 1: An Immunological Prespective", *Ann. Rev. Immunol.* 3:263 (1985).
March et al., "Cloning, Sequence and Expression of Two Distinct Human Interleukin—1 Complementary DNAs", *Nature* 315:641 (1985).
Knudsen et al., "Purification and Characterization of a Unique Human Interleukin 1 From the Tumor Cell Line U937", *J. Immunol.* 136:3311 (1986).
Matsushime et al., *Cell Immunol* 92, 1985, pp. 290–301.
Lomelico et al., *Nature* 312, 1984, pp. 458–462.
Gray et al., *J. Immunol,* vol. 137, 1986, pp. 3644–3648.
Windele et al. J. Immunol 132(3) 1984, pp. 1317–1323.
Furutoni et al. *N. A. Res* 14(8) 1986, pp. 3167–3178.
Clark et al., *N.A. Res* 14(20) 1986 pp. 7897–7914.
Krakaner et al. CA, vol. 102, 1985, #219322g.
Prestidge et al. CA, vol. 102, 1985 #77013p.
Mezel et al., *J. Immunol* 126(3) 1981, pp. 834–837.
Cameron et al., J Exp Med 162, 1985, pp. 790–801.
Cameron et al., J Exp Med 164, 1986 pp. 237–250.
Sofen et al *Biotechniques* Nov.–Dec., 1983, pp. 198–203.
Matsushima et al. *Biochemistry* 25(12) 1986, pp. 3424–3429.
Bonneyea et al. *Bio Technology* vol 4, 1986, pp. 954–958.
Kronheim et al *J. Exp. Med* 161, 1985, p. 490.
Rimsky et al, *J. Immunol* 136, 1986, p. 3304.

*Primary Examiner*—Howard E. Schain
*Assistant Examiner*—Garnette D. Draper
*Attorney, Agent, or Firm*—Scott G. Hallquist; Christopher L. Wight

[57] ABSTRACT

A process is provided for purifying recombinant IL-1 from microbial cells, comprising suspending the cells in an aqueous buffered medium having a pH from about 1 to about 5; disrupting the cells to provide an extract containing solubilized IL-1; and recovering solubilized Il-1 from the extract.

19 Claims, No Drawings

PURIFICATION OF RECOMBINANT INTERLEUKIN-1

BACKGROUND OF THE INVENTION

The present invention relates generally to protein chemistry, and specifically to processes for purifying reoombinant proteins produced by high level expression in microorganisms.

Interleukin-1 (IL-1) is a lymphokine released by macrophages in response to immunogenic stimulation. This polypeptide has been associated with a complex spectrum of biological activities. IL-1 is a primary immunostimulatory signal capable of inducing thymocyte proliferation via induction of interleukin-2 release, and stimulating proliferation and maturation of B-lymphocytes. In addition, IL-1 has been linked with prostaglandin production and induction of fever, and with promotion of wound healing. Reviews of the literature relating to IL-1 include Oppenheim et al., Immunol. Today 7:45 (1986), and Durum et al., Ann. Rev. Immunol. 3:263 (1985).

Human IL-1 activity resides in two distantly related proteins, herein designated IL-1α and IL-1β(March et al., Nature 315:641 (1985)). Both molecules are normally synthesized as larger precursors having molecular weights of about 30,000 daltons, which are subsequently proteolytically processed to yield mature forms having molecular weights of approximately 17,500 daltons.

Recently, cDNAs coding for both human IL-1 species have been cloned and expressed in microorganisms. This achievement should enable production of sufficient quantities of IL-1α and IL-1β to permit therapeutic use. However, difficulties have been encountered in purification of active, nondenatured IL-1 species from cells capable of high level expression of the recombinant proteins. These difficulties have been attributed to the observation that the recombinant protein appears to be concentrated by the producing organisms in an insoluble form.

Gubler et al., J. Immun. 36:2492 (1986) reported a process for crude purification of IL-1α expressed in E. coli. However, this process involved use of the denaturing agents guanidine hydrochloride and urea to enhance solubilization of the recombinant proteins.

The present invention provides a rapid, efficient acid-mediated recombinant protein solubilization process for isolating recombinant IL-1 from microbial cell cultures.

SUMMARY OF THE INVENTION

The present invention provides a process for purifying recombinant IL-1 from microbial cells, comprising:
(a) suspending the cells in an aqueous buffered medium having a pH from about 1 to about 5;
(b) disrupting the cells to provide an extract containing solubilized IL-1; and
(c) recovering solubilized IL-1 from the extract. In a product aspect, the present invention provides purified recombinant IL-1α having a specific activity greater than about $6.0 \times 10^8$ units per mg and endotoxin levels less than 100 pg endotoxin/μg rIL-1α; and purified recombinant IL-1β having a specific activity greater than about $1.9 \times 10^8$ units per mg and endotoxin levels less than about 50 pg endotoxin/μg rIL-1β, where endotoxin levels are measured by a limulus amebocyte lysate assay.

DETAILS OF THE INVENTION

The process of the present invention involves extraction of recombinant human IL-1 species from microbial cells under acid conditions. Acid extraction simultaneously solubilizes the IL-1 and precipitates the bulk of the microbial proteins, enabling recovery of IL-1 in supernatants of the acid extracts. Preliminary experiments have indicated that in E. coli, recombinant IL-1 is expressed in an insoluble form. In general, recombinant proteins can be solubilized with such chaotropic agents as guanidine or urea. In contrast, acid-mediated extraction avoids denaturing extractants, and allows purification to proceed directly from the initial extraction step to subsequent ion exchange procedures without solvent interference or protein denaturation. This process is thus ideally suited for scaling-up to provide commercially significant quantities of recombinant IL-1α and IL-1β.

As used herein, "interleukin-1", "recombinant interleukin-1", "IL-1" and "rIL-1" refer collectively to recombinant forms of IL-1α and IL-1β produced by microbial fermentation processes. In addition, the term comprehends proteins having amino acid sequences substantially identical to that of native mammalian forms of IL-1α and IL-1β, which possess biological activity in common with the native forms. Substantial identity of amino acid sequences means that the sequences are identical or differ by one or more amino acid alterations (deletions, additions, or substitutions) that do not cause an adverse functional dissimilarity between the synthetic protein and the native form.

Preferably, the acid-mediated extraction step for rIL-1α is conducted in an aqueous buffered medium having a pH from about 2.0 to about 3.5, and most preferably, at a pH from about 2.6 to about 3.0. In the case of rIL-1β, the acid extraction step is preferably conducted at a pH from about 3.5 to about 4.5, and most preferably, at a pH from about 3.7 to about 4.1. As used herein, the term "microbial cells" means bacteria, particularly Escherichia coli, and yeast, e.g., Saccharomyces cerevisiae. In the process of this invention, cells can be disrupted by any convenient method, including freeze-thaw cycling, sonication, mechanical disruption, or use of cell lysing agents.

In a more complete process aspect, the acid extraction steps are coupled with subsequent chromatography in aqueous media. This part of the purification process preferably includes an initial ion exchange chromatography stage followed by affinity chromatography. The ion exchange stage comprises, in a preferred aspect, cation exchange chromatography followed by anion exchange chromatography.

Suitable cation exchange chromatography media include various insoluble matrices comprising sulfopropyl or carboxymethyl groups. Sulfopropyl groups are preferred. The matrices can be acrylamide, agarose, dextran, cellulose or other ion exchange resins or substrates commonly employed in protein purification. A particularly useful material for cation exchange chromatography of rIL-1α and rIL-1β is Sulphopropyl Sephadex C-25 (Pharmacia Fine Chemicals, Uppsala, Sweden). When media containing sulfopropyl groups are employed, extracts containing rIL-1 species are applied at a pH of about 4.0, in a suitable buffer such as sodium citrate. rIL-1 species are bound by the ion exchanger, and can be eluted in more highly purified form by application of a weakly basic eluant, for example, 10 mM Tris-HCl, pH 8.1.

Suitable anion exchange chromatography media include various insoluble matrices comprising diethylaminoethyl(DEAE) or diethyl-(2-hydroxypropyl) aminoethyl (QAE) groups. DEAE groups are preferred. The matrices can be acrylamide, agarose, dextran, cellulose or other types commonly employed in protein purification. A particularly useful material for anion exchange chromatography of rIL-1α and rIL-1β is DEAE-Sephacel (Pharmacia). When media containing DEAE groups are employed, extracts containing rIL-1 species are applied at a weakly basic pH. For example, the pooled rIL-1-containing fractions resulting from the previous cation exchange chromatography step (at a pH of about 8.1) can be applied directly in a suitable buffer such as Tris-HCl. rIL-1 species are bound by the anion exchange media, and can be eluted in more highly purified form by application of a salt gradient in the same buffer. It has been determined that rIL-1α elutes from DEAE-Sephacel at 0.17–0.22 M NaCl, and rIL-1β at 0.075–0.155 M NaCl. Thus, gradients ranging from 0 to 600 mM NaCl and 0 to 400 mM NaCl are useful in purifying rIL-1α and rIL-1β, respectively.

In its most preferred aspects, the invention provides a process including the foregoing extraction and ion-exchange chromatography procedures followed by affinity chromatography. For IL-1α, affinity media comprising pendant phenyl glycidyl ether groups (or other groups providing a pendant phenyl nucleus attached by an ether or amide bridge to a suitable substrate) are preferred. Such media include, for example, Phenyl Sepharose CL-4B (Pharmacia) although other insoluble matrices, for example dextran or cellulose derivatives, could be employed. rIL-1α is applied to such media in a solution containing about 0.5 to 0.7 M, and preferably, about 0.6 M ammonium sulfate, in a suitable buffer at a pH of about 8.1, and then eluted with a decreasing linear gradient of ammonium sulfate followed by buffer containing no salt. rIL-1α elutes from Phenyl Sepharose CL-4B at about 0.25–0.10 M ammonium sulfate.

Thus, for IL-1α, the most preferred process comprises suspending microbial cells having associated recombinant IL-1α in an aqueous buffered medium having a pH from about 2.0 to about 3.5; disrupting the cells to extract solubilized IL-1α; applying the solubilized IL-1α to cation exchange media at a pH from about 2.5 to about 5.0; eluting the IL-1α from the cation exchange media at a pH from about 7.5 to about 9.0; applying the IL-1α to anion exchange media in a buffer having low osmolarity; eluting the IL-1α in a gradient of increasing salt concentration; applying the IL-1α, in a buffer containing 0.5 to 0.7 M ammonium sulfate, to media comprising pendant phenyl glycidyl ether groups, and eluting the IL-1α in a gradient of decreasing ammonium sulfate concentration. The resulting fractions can be concentrated by a final chromatography step on media containing pendant sulfopropyl groups.

For the final affinity step for purifying IL-1β, affinity media comprising pendant triazinyl red dye ligand groups are preferred. Such media include those having pendant groups

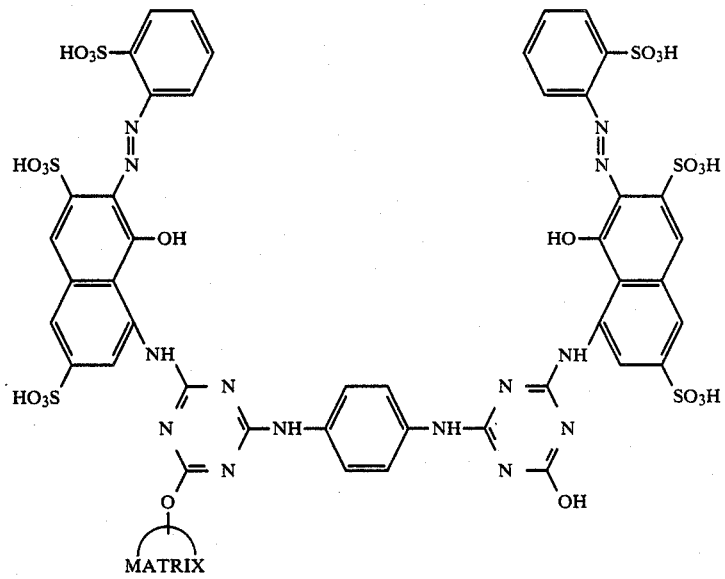

formed by conjugation of certain sulfonated naptholine dye species known as Procion Red or "reactive red", with appropriate insoluble substrates. Commercially available materials meeting these criteria include Red Sepharose CL-6B (Pharmacia), reactive red-agarose (Sigma Chemical Company, St. Louis, Mo., U.S.A.) and Procion Red agarose (Bethesda Research Laboratories, Gaithersburg, Md. U.S.A.) Preferably, pooled fractions containing rIL-1β are applied to the dye-ligand media at a low ionic strength, e.g., less than 40 mM, in a suitable buffer such as 10 mM Tris-HCl. The media comprising bound rIL-1β is then washed with additional application buffer, and the desired protein eluted in a linear gradient of increasing salt concentration, e.g., 0 to 1 M NaCl. rIL-1β elutes from Procion Red at about 0.36–0.46 M NaCl. The resulting fractions can be concentrated by a final chromatography step on media containing pendant sulfopropyl groups.

Thus, for rIL-β, the most preferred process comprises suspending microbial cells having associated recombinant IL-1β in an aqueous buffered medium having a pH from about 3.5 to about 4.5; disrupting the cells to extract solubilized IL-1β; applying the solubilized IL-1β to cation exchange media at a pH from about 2.5 to about 5.0; eluting the IL-1β from the cation exchange media at a pH from about 7.5 to about 9.0; applying the IL-1β to anion exchange media in a buffer having low ionic strength; eluting the IL-1β in a gradient of increasing salt concentration; applying the IL-1β to media comprising pendant Procion Red dye ligand groups; and eluting the IL-1β in a gradient of increasing sodium chloride concentration.

1. Assays for IL-1 Activity and Endotoxin Levels

Progress of rIL-1α or rIL-1β purification can be monitored by a thymocyte mitogenesis assay, which involves ascertaining the capacity of a sample to induce proliferation of thymocytes from CD-1 mice. In this assay, approximately $1 \times 10^6$ thymocytes, obtained from 10 to 12 week old CD-1 mice (Charles River Breeding Laboratories, Wilmington, MA) are seeded in round bottom microplate wells (Corning Plastics, Corning, N.Y.) in the presence of three-fold serial dilutions of the IL-1 containing fluid samples. The thymocytes are cultured in 150 μl of Eagle's minimal essential medium (MEM) containing 50 U/ml penicillin, 50 μg/ml streptomycin, 2 mM glutamine, 0.2 mM gentamycin, 10 mM HEPES (N-2-Hydroxyethylpiperazine-N'-2-ETHANESULFONIC ACID) BUFFER, PH 7.4, TOGETHER WITH 4% w/v human serum and $10^{-5}$ M 2-mercaptoethanol. The samples are cultured for 72 hours at 37° C. in an atmosphere of 5% $CO_2$ in air. Thereafter, the cultures are pulsed for approximately 4 hours with 0.5 microcuries (μCi) of tritiated thymidine ($^3$H-Tdr) after which the cultures are harvested onto glass fiber filter strips with the aid of a multiple-automated sample harvester. Details of this procedure are provided by Gillis et al., *J. Immun.* 120:2027 (1978) and in U.S. Pat. No. 4,411,992.

In this assay, only the CD-1 cells cultured in the presence of IL-1 incorporate $^3$H-Tdr in a dose-dependent manner. CD-1 cells cultured in the absence of IL-1 incorporate only background levels of radiolabel. IL-1 activity is calculated from the linear portion of the $^3$H-Tdr incorporation data. Units of IL-1 activity are determined as the reciprocal dilution of a sample which generates 50% of maximal thymocyte $^3$H-Tdr incorporation as compared to a laboratory standard.

Alternatively, IL-1 activity can be assayed by an IL-1 conversion assay, which relies upon the discovery that IL-1 converts an IL-2 nonproducer cell line, the murine tumor cell line LBRM-33-145, to an IL-2 producer. In this assay, LBRM-33 -1A5 cells, (ATCC No. CRL-8079) are inactivated by addition of 50 μg/ml mitomycin C and incubated for one hour at 37° C. 100 μl of the inactivated cells ($5 \times 10^5$ cells/ml) are cultured in 96-well flat-bottomed plates in the presence of an equal volume of the mitogen, phytohemagglutinin (PHA, 1%) together with serial dilutions of samples. At hourly time intervals the existence of IL-2 activity generated by IL-1 triggered, mitomycin C-inhibited LBRM-33-1A5 cells is directly ascertained by adding 50 μl of IL-2 dependent CTLL-2 cells ($8 \times 10^4$ cells/ml). The microwell cultures are then incubated for 20 additional hours followed by a 4 hour pulse with 0.5 μCi of $^3$H-Tdr, and the resulting pulsed cultures assayed for thymidine incorporation as detailed above. Only the CTLL-2 cells added to wells previously contacted with IL-1 (thereby inducing IL-2 production in the inactivated LBRM cells) will incorporate radiolabel. This conversion assay is both more rapid and more sensitive than the thymocyte mitogenesis assay.

Protein concentrations can be determined by any suitable method. However, the Bio-rad total protein assay (Bio-rad Laboratories, Richmond, Calif. USA) is preferred. SDS-PAGE can also be employed to monitor purification progress, substantially as described by Kronheim et al., *J. Exp. Med.* 161:490 (1985) or other suitable technique. Additional details regarding use of the IL-1 assays described above are disclosed by Conlon, *J. Immun.* 131:1280 (1983) and Kronheim et al., supra.

Endotoxin levels are conveniently assayed using a commercial kit available from Whittaker Bioproducts, Walkersville, Md., U.S.A., (Quantitative Chromogenic Lal QCL-1000) or its equivalent. This method uses a modified limulus amebocyte lysate and synthetic color-producing substrate to detect endotoxin chromogenically. Purified rIL-1α and rIL-1β are tested for presence of endotoxin at multiple dilutions. The assay is preferably performed shortly following completion of purification and prior to storage at −70° C. To minimize the possibility of bacterial contamination during the purification process itself, sterile buffers are preferably employed.

2. Production of rIL-1α and rIL-1β

A. Construction of bacterial expression vectors

Mature IL-1α and IL-1β can be expressed in *E. coli* under the control of the phage λ PL promoter and cI857ts thermolabile repressor. Expression plasmids for rIL-1α and rIL-1β production can be constructed from plasmid pPLc28 (ATCC 53082), plasmid pKK223-3 (available commercially from Pharmacia Fine Chemicals, Uppsala, Sweden) and plasmids containing IL-1α clone 10A (March et al., supra; ATCC 39997) and IL-1β clone IL-1-14 (ATCC 39925) as follows.

To create an expression vector for IL-1α, a 3' portion of the IL-1α gene, extending from Ser$^{113}$ (nucleotides 337–339) to Ala$^{271}$ (nucleotides 811–813) is inserted into expression vector pPLc28. This is achieved by excising a 499 base pair AluI-NdeI fragment from the 10A clone, to which the following synthetic oligonucleotide linker is joined:

```
AATTCTAGGATAATTA ATG TCA GCA CCT TTT AG
    GATCCTATTAAT TAC AGT CGT GGA AAA TC
```

This linker includes AluI and EcoRI termini, a ribosome binding site, and ATG initiation codon in addition to the IL-1α Ser$^{113}$-Ser$^{117}$ sequence. pPLc28 is then digested to completion with EcoRI and NdeI, and the resulting larger fragment isolated by agarose gel electrophoresis. The linker, 10A clone, and plasmid fragments are then fused using T4 ligase, to provide an expression plasmid herein denoted pILPα. Additional details of the construction of pILPα can be found in the disclosure of copending, commonly assigned U.S. patent application Ser. No. 721,765, the disclosure of which is incorporated by reference herein.

The resulting construct is then employed to transform *E. coli* strain ΔH1 (ATCC 33767; Castellazi et al., *Molec. gen. Genet.* 117:211) to ampicillin resistance, using standard techniques. To express the plasmid-borne IL-1α gene, cultures of transformed ΔH1 are grown in L-broth without ampicillin. When the cultures reach an $A_{720}$ of about 0.5, the culture temperature is raised to about 42° C. to promote derepression of the thermolabile PL promoter. After one hour at elevated temperature, cells are harvested by centrifugation and flash-frozen in a dry-ice/methanol mixture. IL-1α activity in cell extracts can be assayed by either the thymocyte mitogenesis or IL-1 conversion assays previously described. Details regarding purification procedures are provided in the following Examples.

rIL-1β can be produced via construction of an plasmid, herein designated pILPβ. This vector is assembled from pILPc (March et al., supra), which is constructed by replacing the BamHI/EcoRI fragment of pKK223-3 with a Sau3A/EcoRI fragment from pPLc28 containing the λ PL promoter. This plasmid is digested to completion with EcoRI and PstI, and the largest fragment then ligated to a (1) a 669 base pair HpaII/PstI fragment from pIL-1-14 (ATCC 39925) containing the human IL-1β gene (Ala117 to COOH terminus encodes active protein) and (2) the following EcoRI/HpaI synthetic oligonucleotide:

```
AATTCTAGGATAATTA ATG GCA CCT GTA CGA TCA CTG AAC TGC ACG CTC
    GATCCTATTAAT TAC CGT GGA CAT GCT AGT GAC TTG ACG TGC GAG GC
```

Plasmid pILPβ is then used to transform E. coli H1 or other cells containing a thermolabile repressor of PL transcription. Following growth to $A_{720}$ of about 0.5, expression of the rIL-1β gene is obtained by heat induction as previously described. rIL-1β activity, as in the case of rIL-1α, can be identified using the thymocyte mitogenesis or IL-1 conversion assays cited above.

EXAMPLES 1 AND 2: PROTEIN PURIFICATION

The general purification scheme described in Examples 1 and 2, below, involved an initial acid extraction from cell pellets, followed by an SPS (Sulphopropyl Sephadex; Pharmacia) column chromatography step and elution from a DEAE-Sephacel (Pharmacia) column. Column fractions containing rIL-1α were then applied to Phenyl Sepharose CL-4B (Pharmacia), while those containing rIL-1β were applied to a Procion Red agarose (Bethesda Research Laboratories) column for final purification. Sterile buffers were used throughout the purification protocol to safeguard the product from contamination by endotoxin. Chromatography fractions were monitored for protein concentration by the Biorad total protein assay (Bio-rad Laboratories, Richmond, Calif., USA) and the progress of purification evaluated by SDS-PAGE as described by Kronheim, J. Exp. Med. 161:490 (1985). IL-1 activity of column fractions was determined by the IL-1 assays previously referenced.

Experiments in which the pH of the initial extraction buffer was varied indicated that extraction of rIL-1α from E. coli cell suspensions at pH 2.8 resulted in precipitation of significant quantities of contaminating proteins while enabling good recovery of rIL-1α. Similar experiments involving rIL-1β indicated that pH 3.9 is optimal for precipitating unwanted proteins while solubilizing rIL-1β. Thus, the optimal pH for this initial extraction step may vary between fermenter batches. For this reason, small-scale pilot runs may be employed to determine optimal pH, particularly where large quantities of material are involved.

rIL-1α and rIL-1β were produced by growth and derepression of appropriate E. coli cells harboring high level thermolabile expression plasmids for rIL-1α and rIL-1β. Cells were grown in a 10 liter Microferm Fermentor (New Brunswick) employing conditions of maximum aeration and vigorous agitation. An antifoaming agent (Antifoam A) was employed. Cultures were grown at 30° C. in the super induction medium disclosed by Mott et al., Proc. Natl. Acad. Sci. USA 82:88 (1985) plus antibiotics, derepressed at a cell density corresponding to $A_{600}$=0.05 by elevating the temperature to 42° C. and harvested 16 hours after the upward temperature shift. The cell mass was initially concentrated using the Pellicon Cassette System (Millipore). The cell slurry was then centrifuged at 10,000 ×g for 10 minutes at 4° C. followed by rapid freezing of the cell pellets from 2.5 liter culture aliquots.

To achieve the initial acid extraction, cell pellets obtained from 2.5 liters fermentation medium as described above were suspended in about 20 ml 30 mM Tris-HCl buffer, pH 8, containing 5 mM EDTA and 1 mM phenylmethylsulfonyl fluoride (PMSF). The resulting suspension was rapidly frozen in a dry ice/methanol bath and then thawed. Next, 200 ml of 30 mM sodium citrate buffer at pH 2.8 (rIL-1α) or 3.9 (rIL-1β), containing 5 mM EDTA and 250 µg/ml lysozyme was added to the suspensions. The resulting acid suspensions were incubated for 60 minutes in a 37° C. water bath. Following incubation, the extracts were rapidly frozen in a dry-ice/methanol bath, thawed, and then centrifuged at 4° C. for 45 minutes at 38,000 ×g. Supernatants were then carefully decanted for use in the next purification step.

Extraction of rIL-1α from the E. coli cell suspension at pH 2.8 resulted in the precipitation of 79% of the contaminating proteins and recovery of 62.5% of the rIL-1α. The resulting extract was applied to an SPS C-25 column at pH 4. The column had been preconditioned with 0.1% Triton X-100 (polyoxyethylene ether; Sigma Chemical Company, St. Louis, Mo., USA) and 10% fetal calf serum to reduce nonspecific absorption of IL-1 activity to the resin. First, the pH of the crude extract was raised to about 4.0 by addition of 1.0 N NaOH, and then the resulting solutions were applied to 20×2.5 cm columns containing SPS C-25, previously equilibrated with 10 mM sodium citrate, pH 4.0. The column was washed with 3 column volumes 10 mM 2-(N-morpholino)ethanesulfonic acid (MES) buffer, pH 5.0, and desired protein eluted from the column with 10 mM Tris-HCl, pH 8.1. 10 ml fractions were collected, analyzed by SDS-PAGE, and stored at 4° C. for additional purification. The elution with 10 mM Tris-HCl buffer at pH 8.1 resulted in a pH rise after 3 column volumes and elution of the rIL-1α, while 49% of the contaminating proteins remained bound to the gel.

Fractions containing IL-1 activity from the previous step were combined and then applied to a 15×2.5 cm column containing DEAE-Sephacel previously equilibrated with 10 mM Tris-HCl pH 8.1. Since rIL-1α was eluted from the SPS column in the equilibration buffer of the DEAE column, the SPS pool (200-250 ml) could be loaded directly onto the DEAE column, avoiding loss of activity by dialysis. The DEAE column was washed with five column volumes of the starting buffer and then eluted with linear gradient of 0 to 600 mM NaCl in 10 mM Tris-HCl, pH 8.1, in a total of two column volumes. 5 ml fractions were collected, analyzed by SDS-PAGE, and held at 4° C. for further purification. rIL-1α eluted from the column at 0.17-0.22

M NaCl. 66% of the contaminating proteins were eliminated in this step; 20% eluted earlier in the salt gradient and 46% remained bound to the gel after elution of rIL-1α.

Fractions containing rIL-1α were pooled (50–60 ml) and treated by addition of sufficient solid ammonium sulfate to provide a final concentration of 0.5 M. The resulting solution was then applied to a 30×2.5 cm column containing Phenyl Sepharose CL-4B, equilibrated with 10 mM Tris-HCl buffer, also 0.5 M in ammonium sulfate, at pH 8.1. The column was washed with 5 column volumes starting buffer, and eluted with a decreasing linear gradient of ammonium sulfate starting at 0.5 M and ending at 0 M in about 3 column volumes. Finally, the column was eluted with about 100 ml 10 mM Tris-HCl, pH 8.1. rIL-1α eluted at about 0.25–0.10 M ammonium sulfate. 10 ml fractions were collected. PAGE of the fractions indicated that the Phenyl Sepharose step purified rIL-1α to homogeneity. Those fractions containing rIL-1α were pooled and concentrated by reapplication to SPS C-25 as described by Kronheim et al., supra. rIL-1α was eluted using 10 mM phosphate buffered saline (PBS) at pH 8.2.

Purified rIL-1α was stored at −70° C. The purified rIL-1α contained only about 60 pg endotoxin per μg IL-1α, and exhibited a specific activity of $6.5 \times 10^8$ units per mg. Overall yield for fermentation and purification was about 16.8 mg purified rIL-1α per liter culture.

Extraction of rIL-1β from the *E. coli* cell suspension at pH 3.9 resulted in precipitation of 69% of the contaminating proteins and recovery of 37.3% of the rIL-1β activity. Extracts containing rIL-1β were also applied to an SPS C-25 column which had been pretreated with 0.1% Triton X-100 (polyoxyethylene ether; Sigma Chemical Company, St. Louis, Mo., USA) and 10% fetal calf serum. Protein was applied and eluted substantially as described for rIL-1α, above. This SPS step removed 68% of the contaminating protein with good recovery of rIL-1β.

Fractions containing rIL-1 activity from the SPS step were combined and then applied to 15×2.5 cm columns containing DEAE-Sephacel previously equilibrated with 10 mM Tris-HCl pH 8.1. As described for rIL-1α, above, the DEAE columns were washed with five column volumes of the starting buffer and then eluted with linear gradients of 0 to 400 mM NaCl in a total of two column volumes. rIL-1β eluted from the DEAE column at 0.075 M to 0.155 M NaCl, absent 62% of the contaminating proteins.

Fractions containing rIL-1β resulting from the DEAE column step were diluted 1:4 in 10 mM Tris-HCl buffer, pH 8.1, to reduce ionic strength to less than 40 mM, then applied to a 20×2.5 cm column containing Procion Red agarose previously equilibrated with 10 mM Tris-HCl buffer, pH 8.1. The column was washed with five column volumes of starting buffer, and then eluted with a linear gradient in five column volumes ranging from 0 to 1 M NaCl in 10 mM Tris-HCl buffer, pH 8.1. Fractions of 10 ml were collected, analyzed, and then concentrated as described for rIL-1α, above. rIL-1β eluted from the Procion Red column at 0.36–0.46 M NaCl.

Purified rIL-1β thus obtained exhibited a specific activity of $1.95 \times 10^8$ units per mg, and contained only 36 pg endotoxin per μg rIL-1β. Overall yield of protein was about 85.2 mg purified protein per liter culture.

The results of the purification procedures described above are summarized in Table 1, below.

TABLE 1

Purification of Recombinant IL-1α and IL-1β

| | Total Protein (mg) | Total Activity (U × $10^{10}$) | Yield (%) | Specific Activity (U/mg × $10^7$) |
|---|---|---|---|---|
| A. IL-1α: | | | | |
| Cell Suspension | 4576 | 8.0 | 100 | 1.7 |
| Cell Extract | 968 | 5.0 | 62.5 | 5.1 |
| SPS Pool | 493 | 5.0 | 62.5 | 5.1 |
| DEAE Sephacel pool | 168 | 2.45 | 30.6 | 15.0 |
| Phenyl Sepharose pool | 42 | 2.73 | 34.1 | 65.0 |
| B: IL-1β | | | | |
| Cell suspension | 10116 | 19.3 | 100 | 1.9 |
| Cell extract | 3096 | 7.2 | 37.3 | 2.3 |
| SPS pool | 978 | 13.2 | 68.7 | 13.5 |
| DEAE-Sephacel pool | 376 | 5.6 | 29.0 | 14.8 |
| Procion Red pool | 213 | 4.16 | 21.6 | 19.5 |

What is claimed is:

1. A process for purifying recombinant IL-1 from microbial cells, comprising:
   (a) suspending the microbial cells in an aqueous buffered medium having a pH from about 1 to about 5;
   (b) disrupting the microbial cells to provide an extract containing solubilized recombinant IL-1; and
   (c) recovering solubilized recombinant IL-1 from the extract.

2. A process according to claim 1, wherein the recombinant IL-1 is IL-1α.

3. A process according to claim 2, wherein the cells are suspended in an aqueous buffered medium having a pH from about 2.0 to about 3.5.

4. A process according to claim 3, wherein the cells are suspended in an aqueous buffered medium having a pH from about 2.6 to about 3.0.

5. A process according to claim 1, wherein the recombinant IL-1 is IL-1β.

6. A process according to claim 5, wherein the cells are suspended in an aqueous buffered medium having a pH from about 3.5 to about 4.5.

7. A process according to claim 6, wherein the cells are suspended in an aqueous buffered medium having a pH from about 3.7 to about 4.1.

8. A process according to claim 1, wherein solubilized IL-1 is recovered from the extract by ion exchange or affinity chromatography in aqueous media.

9. A process according to claim 8, wherein the chromatography comprises ion exchange chromatography.

10. A process according to claim 9, wherein the chromatography further comprises affinity chromatography.

11. A process according to claim 10, wherein the ion exchange chromatography includes a cation exchange step comprising applying the IL-1 to cation exchange media under acidic conditions, followed by elution under weakly basic conditions.

12. A process according to claim 11, wherein the cation exchange step is followed by an anion exchange step comprising applying the IL-1 to anion exchange media in a low osmolarity buffer, followed by elution in a gradient of increasing salt concentration.

13. A process according to claim 12, wherein the recombinant IL-1 is IL-1α.

14. A process according to claim 13, wherein the ion exchange chromatography is followed by an affinity chromatography step comprising application of IL-1α in a buffer containing 0.4–0.6 M ammonium sulfate to media comprising pendant phenyl glycidyl ether groups, and elution in a gradient of decreasing ammonium sulfate concentration.

15. A process according to claim 14, comprising:
   (a) suspending microbial cells having associated recombinant IL-1α in an aqueous buffered medium having a pH from about 2.0 to about 3.5;
   (b) disrupting the cells to extract solubilized IL-1α;
   (c) applying the solubilized IL-1α to cation exchange media at a pH from about 2.5 to about 5.0;
   (d) eluting the IL-1α from the cation exchange media at a pH from about 7.5 to about 9.0;
   (e) applying the IL-1α to anion exchange media in a buffer having low osmolarity;
   (f) eluting the IL-1α in a gradient of increasing salt concentration;
   (g) applying the IL-1α in a buffer containing 0.5–0.7 M ammonium sulfate to media comprising pendant phenyl glycidyl ether groups, and
   (h) eluting the IL-1α in a gradient of decreasing ammonium sulfate concentration.

16. A process according to claim 12, wherein the recombinant IL-1 is IL-1β.

17. A process according to claim 16, wherein the ion exchange chromatography is followed by a dye-ligand affinity chromatography step comprising application of IL-1β to media comprising pendant triazinyl red dye ligand groups, and elution of IL-1β in a gradient of increasing salt concentration.

18. A process according to claim 17, comprising:
   (a) suspending microbial cells having associated recombinant IL-1β in an aqueous buffered medium having a pH from about 3.5 to about 4.5;
   (b) disrupting the cells to extract solubilized IL-1β;
   (c) applying the solubilized IL-1β to cation exchange media at a pH from about 2.5 to about 5.0;
   (d) eluting the IL-1β from the cation exchange media at a pH from about 7.5 to about 9.0;
   (e) applying the IL-1β to anion exchange media in a buffer having low osmolarity;
   (f) eluting the IL-1β in a gradient of increasing salt concentration;
   (g) applying the IL-1β to media comprising pendant triazinyl red dye ligand groups; and
   (h) eluting the IL-1β in a gradient of increasing NaCl concentration.

19. A process according to claim 18, wherein the affinity chromatography media comprises pendant Procion Red dye ligand groups.

* * * * *